(12) United States Patent
Morimoto et al.

(10) Patent No.: US 12,678,060 B2
(45) Date of Patent: Jul. 14, 2026

(54) VENOUS PRESSURE TESTING APPARATUS, NON-TRANSITORY COMPUTER READABLE STORAGE MEDIUM, AND VENOUS PRESSURE TESTING METHOD

(71) Applicant: NIHON KOHDEN CORPORATION, Tokyo (JP)

(72) Inventors: Haruka Morimoto, Tokorozawa (JP); Naoki Kobayashi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1184 days.

(21) Appl. No.: 17/651,631

(22) Filed: Feb. 18, 2022

(65) Prior Publication Data

US 2022/0273182 A1 Sep. 1, 2022

(30) Foreign Application Priority Data

Mar. 1, 2021 (JP) ................................. 2021-031491

(51) Int. Cl.

| | |
|---|---|
| ***A61B 5/021*** | (2006.01) |
| ***A61B 5/00*** | (2006.01) |
| ***A61B 5/022*** | (2006.01) |
| ***A61B 5/023*** | (2006.01) |

(52) U.S. Cl.
CPC .......... *A61B 5/02108* (2013.01); *A61B 5/023* (2013.01); *A61B 5/7275* (2013.01); *A61B 5/742* (2013.01)

(58) Field of Classification Search
CPC ... A61B 5/02108; A61B 5/023; A61B 5/7275; A61B 5/742; A61B 5/704; A61B 5/022
See application file for complete search history.

(56) References Cited

FOREIGN PATENT DOCUMENTS

JP 2019-076120 A 5/2019

*Primary Examiner* — Justin Xu
(74) *Attorney, Agent, or Firm* — McDonald Hopkins LLC

(57) ABSTRACT

A testing apparatus for estimating a central venous pressure by measuring a venous pulse by a sensor at a predetermined measurement position of a target person is equipped with an estimation unit which estimates that the central venous pressure of the target person is lower than a reference venous pressure if the venous pulse is not detected by the sensor at the predetermined measurement position of the target person who assumes a particular posture with which a water-gauge pressure corresponding to a vertical distance between the heart of the target person and a peak point, in the vertical direction, of a vein leading from the heart to the measurement position coincides with the reference venous pressure.

15 Claims, 7 Drawing Sheets

FIG. 5
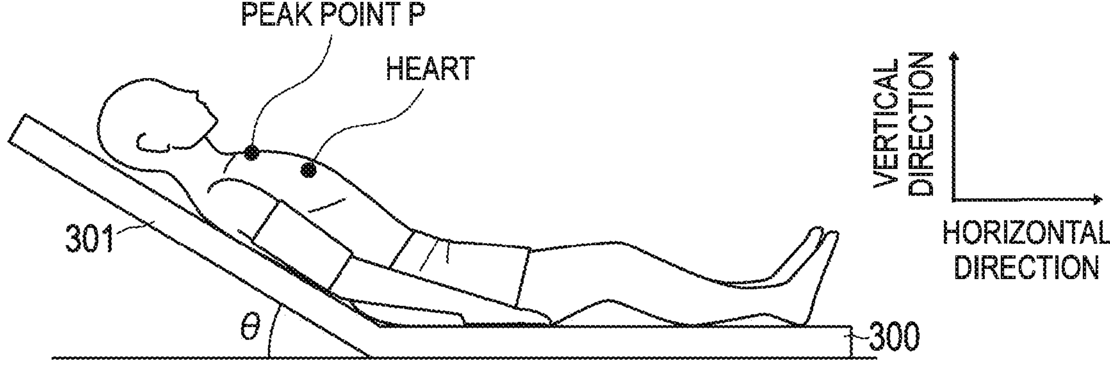
FIG. 6
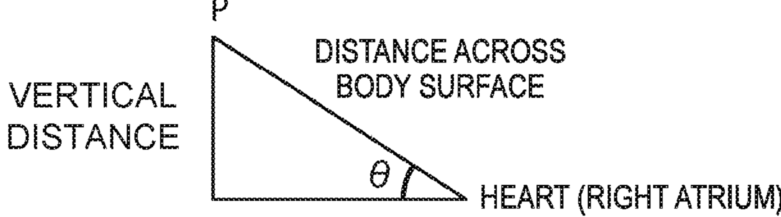
FIG. 7
| REFERENCE VENOUS PRESSURE | ANGLE θ FORMED BY UPPER PART AND LOWER PART OF BODY |
|---|---|
| 2 mmHg | 10° |
| 4 mmHg | 20° |
| 6 mmHg | 30° |
| 7 mmHg | 40° |
| 8 mmHg | 50° |
| 10 mmHg | 60° |

VENOUS PRESSURE TESTING APPARATUS, NON-TRANSITORY COMPUTER READABLE STORAGE MEDIUM, AND VENOUS PRESSURE TESTING METHOD

CROSS-REFERENCE TO RELATED APPLICATIONS

The present application claims priority from Japanese Patent Application No. 2021-031491, filed on Mar. 1, 2021, the entire content of which is incorporated herein by reference.

TECHNICAL FIELD

The presently disclosed subject matter relates to a venous pressure testing apparatus, a non-transitory computer readable storage medium, and a venous pressure testing method.

BACKGROUND ART

A venous pressure in the vicinity of the right atrium, which is called a central venous pressure, is an important index for recognizing circulatory dynamics.

A central venous pressure can be measured invasively by inserting a catheter to the vicinity of the right atrium. On the other hand, in recent years, noninvasive venous pressure testing apparatuses that enable measurement of a central venous pressure and are low in the load of a patient have been being developed.

JP-A-2019-076120 discloses the following prior art technique. Inclination angles of the body longer axis of a measurement target person with respect to the horizontal plane and heartbeat intensity values, corresponding to the respective inclination angles, of an internal jugular vein at a measurement position are measured and stored successively. A boundary inclination angle between a heartbeat detectable range and a heartbeat undetectable range is calculated based on the stored data, and an internal jugular vein pressure is calculated from the calculated inclination angle and a distance from the right atrium to the measurement position.

However, in clinical sites, there is a need to quickly judge only whether a central venous pressure is higher than or lower than a certain reference value. The above-described prior art technique has a problem that it cannot satisfy this need.

SUMMARY

The presently disclosed subject matter has been conceived to solve the above problem, and an object of the presently disclosed subject matter is therefore to provide a venous pressure testing apparatus and a venous pressure testing method that make it possible to estimate quickly whether a central venous pressure is lower than an optional reference value.

The above-mentioned object of the presently disclosed subject matter can be attained by the following means.

A venous pressure testing apparatus for estimating a central venous pressure of a target person by measuring a venous pulse by a sensor at a predetermined measurement position of the target person, comprising an estimation unit which estimates that the central venous pressure of the target person is lower than a predetermined reference venous pressure if the venous pulse is not detected by the sensor at the measurement position of the target person who assumes a particular posture with which a water-gauge pressure corresponding to a vertical distance between the heart of the target person and a peak point, in the vertical direction, of a vein leading from the heart to the measurement position coincides with the reference venous pressure.

A non-transitory computer readable storage medium that stores a venous pressure testing program for testing a central venous pressure of a target person by measuring a venous pulse by a sensor at a predetermined measurement position of the target person, the venous pressure testing program causing a computer to execute processing of estimating that the central venous pressure of the target person is lower than a predetermined reference venous pressure if the venous pulse is not detected by the sensor at the measurement position of the target person who assumes a particular posture with which a water-gauge pressure corresponding to a vertical distance between the heart of the target person and a peak point, in the vertical direction, of a vein leading from the heart to the measurement position coincides with the reference venous pressure.

A venous pressure testing method for estimating a central venous pressure of a target person by measuring a venous pulse by a sensor at a predetermined measurement position of the target person, comprising an estimation step of estimating that the central venous pressure of the target person is lower than a predetermined reference venous pressure if the venous pulse is not detected by the sensor at the measurement position of the target person who assumes a particular posture with which a water-gauge pressure corresponding to a vertical distance between the heart of the target person and a peak point, in the vertical direction, of a vein leading from the heart to the measurement position coincides with the reference venous pressure.

BRIEF DESCRIPTION OF DRAWINGS

FIG. 5 illustrates a particular posture.

FIG. 6 illustrates a vertical distance between the heart and a peak point of the veins.

FIG. 7 is a table illustrating a relationship between the reference venous pressure and the bend angle of a posture guide tool.

DESCRIPTION OF EMBODIMENTS

Figure 1:
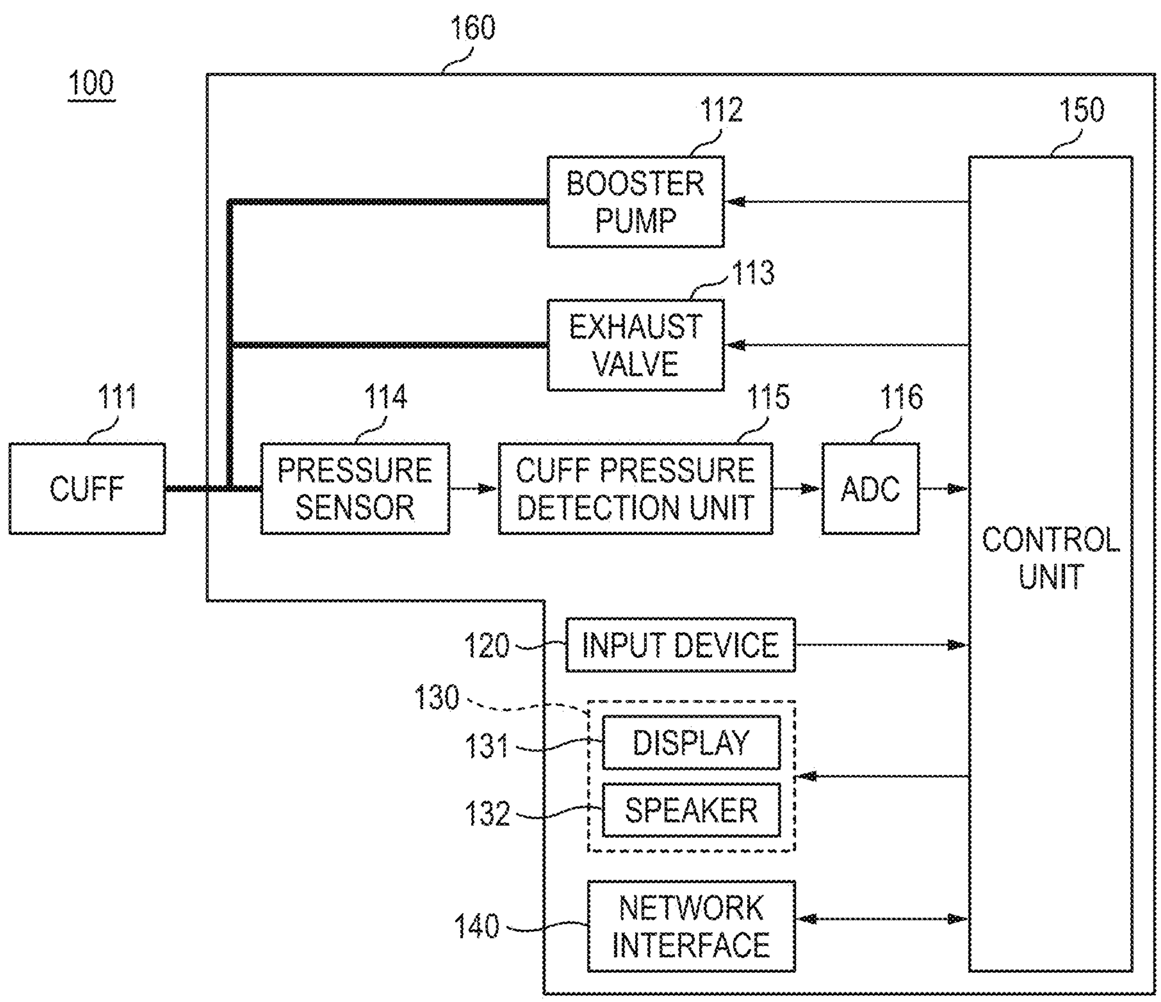
FIG. 1 is a block diagram illustrating a rough hardware configuration of a venous pressure testing system of a First embodiment.

Embodiments of the presently disclosed subject matter will be described in detail by referring to the accompanying drawings. In the drawings, the same members are given the same symbols, respectively. Furthermore, in the drawings, ratios between dimensions may be exaggerated for convenience of description and hence be different from actual ones.

First Embodiment

Figure 2:
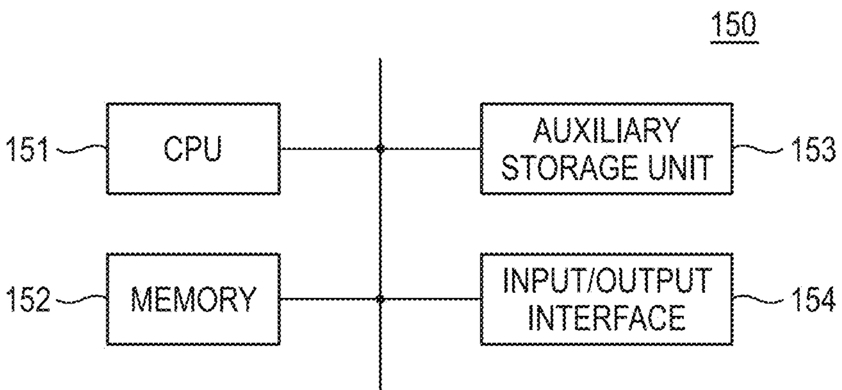
FIG. 2 is a diagram illustrating a rough hardware configuration of a control unit.

FIG. 1 is a block diagram illustrating a rough hardware configuration of a venous pressure testing system 100 according to this embodiment. FIG. 2 is a diagram illustrating a rough hardware configuration of a control unit 150.

The venous pressure testing system 100 is a system for estimating a central venous pressure of a target person. Estimation of a central venous pressure includes, in addition to estimation of a central venous pressure value, estimation as to whether a central venous pressure is higher than or lower than an optional reference value etc. The central venous pressure is an index that reflects a pressure measured in the right atrium (right atrium pressure) and reflects an amount of blood to return to the heart and a preload of the right atrium.

As shown in FIG. 1, the venous pressure testing system 100 can include a cuff 111 and a venous pressure testing apparatus 160. The cuff 111 is configured so as to be able to be connected to the venous pressure testing apparatus 160. The venous pressure testing apparatus 160 can include a booster pump 112, an exhaust valve 113, a pressure sensor 114, a cuff pressure detection unit 115, an AD converter (ADC) 116, an input device 120, output devices 130, a network interface 140, and the control unit 150.

The cuff 111, the booster pump 112, the exhaust valve 113, the pressure sensor 114, the cuff pressure detection unit 115, and the ADC 116 are an example configuration for performing sensing processing for measurement of a venous pulse of a target person and constitutes a sensor.

The cuff 111 is an air bag to be wound around an upper arm of a patient. The booster pump 112 sends air to the cuff 111 according to an instruction from the control unit 150 and thereby increases the pressure in the air bag (called a "cuff internal pressure"). In this manner, the pressure for pressing the upper arm of a patient (hereinafter referred to as a "cuff pressure") by means of the cuff 111 can be increased. The exhaust valve 113 evacuates the cuff 111 gradually by opening the inside of the airbag to the atmosphere and thereby decreases the cuff internal pressure. In this manner, the cuff pressure can be decreased.

The pressure sensor 114 detects a cuff internal pressure. A pulse wave of a patient (hereinafter referred to as a "cuff pulse wave") that occurs in a process that the cuff pressure is increased and decreased is superimposed on a cuff internal pressure. As described later, a cuff pulse wave can have a waveform that is obtained through superimposition of a venous pulse and an arterial pulse. The cuff pressure detection unit 115 extracts, from a detected cuff internal pressure, a cuff pulse wave that is superimposed on it and outputs the cuff internal pressure and the extracted cuff pulse wave to the ADC 116 as analog signals. The ADC 116 converts the analog signals of the cuff internal pressure and the cuff pulse wave into digital signals and sends the latter to the control unit 150. A configuration may be employed that the pressure sensor 114, the cuff pressure detection unit 115, and the ADC 116 are integrated with the cuff 111. A configuration that the pressure sensor 114 and the cuff pressure detection unit 115 are integrated with the cuff 111 and the ADC 116 is provided in the venous pressure testing apparatus 160 is also possible.

The input device 120 receives an input manipulation of a user who has manipulated the venous pressure testing apparatus 160 and generates an input signal corresponding to the received input manipulation. For example, the input device 120 includes a touch panel that is laid on a display 131 of the output devices 130, manipulation buttons attached to the body of the venous pressure testing apparatus 160, a mouse, a keyboard, or the like. The input signal generated by the input device 120 is sent to the control unit 150. The control unit 150 performs predetermined processing according to the input signal. As described later, input manipulations include input of a reference venous pressure. The reference venous pressure is a venous pressure to serve as a reference to be used for judging whether a central venous pressure of a target person is high or low.

The output devices 130 output estimation results of a central venous pressure of a target person. The estimation results include a result of estimation as to whether a central venous pressure of the target person is lower than or higher than or equal to the reference venous pressure. The output devices 130 include the display 131 and a speaker 132. The display 131 can be a liquid crystal display, an organic EL display, or the like that is attached to the body of the venous pressure testing apparatus 160. The display 131 may be a display device to be attached to the head of a user such as a transmission-type or non-transmission-type head-mount display.

The speaker 132 is attached to the body of the venous pressure testing apparatus 160 and can output an estimation result of a central venous pressure in the form of a voice.

The output devices 130 are not limited to the display 131 and the speaker 132 and may be, for example, a printer for printing and outputting an estimation result of a central venous pressure.

The network interface 140 is configured so as to connect the control unit 150 to a communication network. More specifically, the network interface 140 includes processing circuits for various interfaces for communication with external devices over the communication network and is configured to as to be compatible with communication standards for communication over the communication network. Examples of the communication network are a LAN (local area network), a WAN (wide area network), the Internet, etc.

The control unit 150 estimates a central venous pressure of a target person. The control unit 150 may be software or hardware that performs main control on the venous pressure testing apparatus 160 and may be an independent device. For example, the control unit 150 may be either a dedicated medical device for performing a central venous pressure test or a personal computer, a smartphone, a tablet terminal, or the like in which programs for performing a central venous pressure test are installed. As a further alternative, the control unit 150 may be a wearable device or the like that can be attached to the body (e.g., upper arm) of a target person.

The details of the functions of the control unit 150 will be described later.

As shown in FIG. 2, the control unit 150 may include a CPU (central processing unit) 151, a memory 152, an auxiliary storage unit 153, and an input/output interface 154.

The memory can include a ROM (read-only memory) and a RAM (random access memory). The ROM is stored with various programs, various parameters, etc. The RAM has a work area for storing various programs to be run by the CPU 151. The CPU 151 is configured so as to develop, on the RAM, specified ones of various programs stored in the ROM and the auxiliary storage unit 153 and perform various kinds of processing by cooperating with the RAM.

The auxiliary storage unit 153 can be equipped with a storage device (storage) such as an HDD (hard disk drive), an SSD (solid-state drive), or a USB flash memory. The auxiliary storage unit 153 is stored with various programs, various parameters, etc. Furthermore, the auxiliary storage unit 153 stores an estimation result of a central venous pressure.

The input/output interface 154 functions as an interface between the CPU 151, the input device 120, and the output devices 130. The input/output interface 154 can include various communication modules for performing communication with the input device such as a mouse or a keyboard, drive modules for driving the display 131 and the speaker 132, etc.

By causing the CPU 151 to run programs, the control unit 150 controls the individual units of the venous pressure testing system 100 and thereby realizes various functions.

Figure 3:
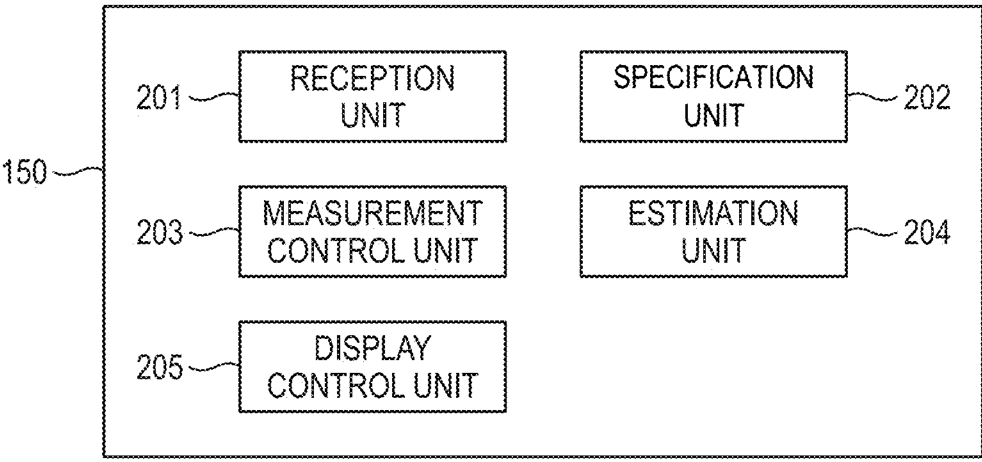
FIG. 3 is a block diagram illustrating functions of the control unit.

FIG. 3 is a block diagram illustrating functions of the control unit 150. The control unit 150 functions as a reception unit 201, a specification unit 202, a measurement control unit 203, an estimation unit 204, and a display control unit 205. The measurement control unit 203 constitutes a setting unit.

The reception unit 201 receives a reference venous pressure (a reference venous pressure value) that has been input to the input unit 120. The reference venous pressure is input to the input unit 120 by a user (or target person). For example, the reference venous pressure is input according to circulatory dynamics that a user who is a healthcare professional desires to check. For example, for the purpose of systemic congestion diagnosis, “10 mmHg” can be input as a reference venous pressure.

The specification unit 202 determines a particular posture for estimation as to whether a central venous pressure of a target person is lower than or higher than or equal to the reference venous pressure based on the reference venous pressure.

Figure 4:
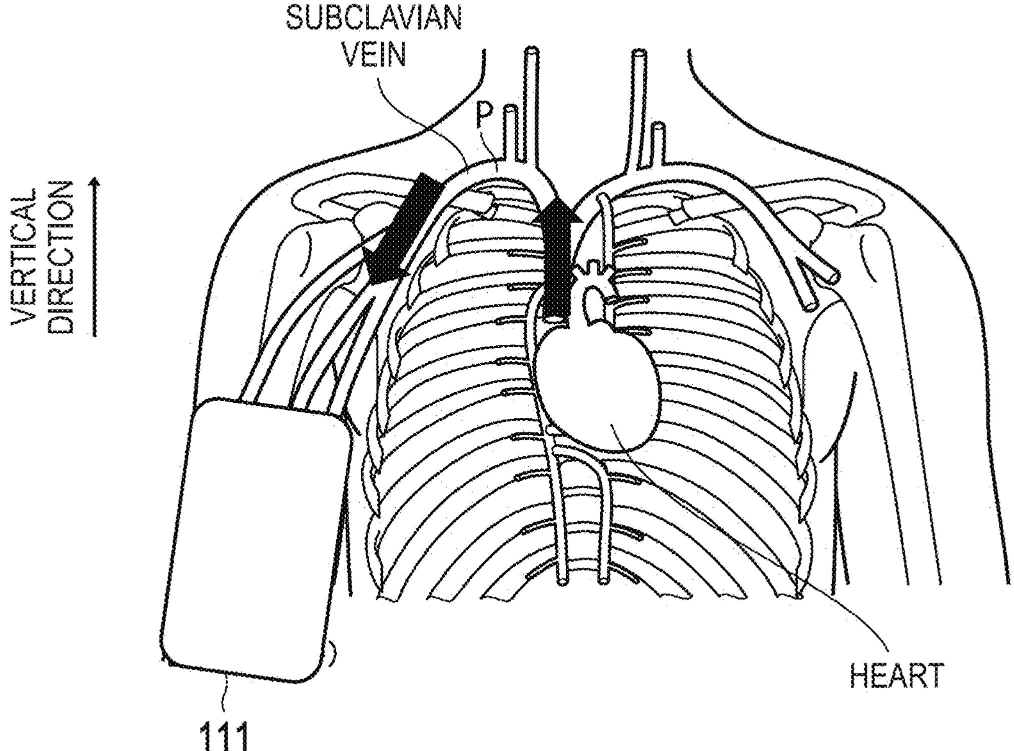
FIG. 4 illustrates veins that lead from the heart to an upper arm.

FIG. 4 illustrates veins that lead from the heart to an upper arm. FIG. 5 illustrates a particular posture. FIG. 6 illustrates a vertical distance between the heart and a peak point P of the veins (hereinafter also referred to simply as a “vertical distance”).

As indicated by thick arrows in FIG. 4, a vein signal (venous pulse) that is output from the heart (right atrium) can reach the veins (right upper arm veins etc.) of the upper arm that is a measurement position and to which the cuff 111 is attached past the right subclavian vein. Thus, a cuff pulse wave detected by the cuff 111 can include a venous pulse. In the following, detection of a cuff pulse wave including a venous pulse is also referred to simply as detection of a venous pulse. However, the veins that lead from the right atrium to the upper arm has a peak point P in the vertical direction near the right subclavian vein. The peak point is a highest point in the vertical direction of veins from the atrium to the measurement position (in the example shown in FIG. 5, upper arm) of a target person who assumes a predetermined posture. Thus, for a venous pulse to be detected at the upper arm (measurement position), venous blood that is output from the heart needs to go over the peak point. That is, a venous pulse is detected at the upper arm only when the central venous pressure is higher than or equal to a water-gauge pressure corresponding to a vertical distance.

A posture guide tool 300 is a tool capable of adjusting the angle θ formed by the upper part and the lower part of the body of a target person by bending a back contact surface 301 that is in contact with the back of the target person. The example of FIG. 5 shows a bed as an example of the posture guide tool 300. The posture guide tool 300 may be a tool other than a bed, such as a chair. The angle θ formed by the upper part and the lower part of the body (i.e., posture) of a target person whose arms hang down can be adjusted by bending the back contact surface 301 that is in contact with the back of the target person lying on his or her back on the posture guide tool 300.

As shown in FIG. 6, a distance across the body surface of a target person (hereinafter also referred to simply as a “body surface distance”) between points corresponding to the heart (more specifically, right atrium) and a peak point P, respectively, on the body surface of the target person is measured in advance as a distance between the heart of the target person and the peak point. A bend angle of the posture guide tool 300 (i.e., an angle θ formed by the upper part and the lower part of the body of the target person) when the vertical distance between the heart and the peak point P corresponds to the reference venous pressure can be calculated by substituting the measurement value into the Pythagorean theorem. That is, an angle θ formed by the upper part and the lower part of the body of the target person whose arms hang down can be specified as a particular posture based on the length (body surface distance) of a line segment connecting points corresponding to the heart and the peak point P on the body surface of the target person, respectively, and an angle formed by this line segment and the horizontal direction (this angle corresponds to a bend angle of the posture guide tool 300). A vertical distance corresponds to the reference venous pressure when a water-gauge pressure corresponding to this vertical distance approximately coincides with the reference venous pressure.

A body surface distance may be calculated using a corresponding relationship between the body surface distance and the body information (e.g., an approximate equation determined through calculation based on sample data of the corresponding relationship between the body surface distance and the body information of plural persons) by calculating the corresponding relationship in advance and storing it in the auxiliary storage unit 153 and receiving body information of a target person additionally by the reception unit 201. For example, the body information includes a height, a gender, a physique (large-framed or small-framed), etc.

FIG. 7 is a table illustrating a relationship between the reference venous pressure and the bend angle of the posture guide tool 300. In the example of FIG. 7, the body surface distance is assumed to be 15 cm.

For example, when the bend angle of the posture guide tool 300 is 15°, the reference venous pressure is calculated to be 2.9 mmHg (15·sin 15°=3.89 cm, 3.89 $cmH_2O$=2.9 mmHg). When the bend angle of the posture guide tool 300 is 30°, the reference venous pressure is calculated to be 5.6 mmHg (15·sin 30°=7.5 cm, 7.5 $cmH_2O$=5.6 mmHg).

In this manner, the specification unit 202 specifies, as a particular posture, an angle θ formed by the upper part and the lower part of the body of the target person.

The measurement control unit 203 bends the back contact surface 301 of the posture guide tool 300 by transmitting a control signal to the posture guide tool 300 (see FIG. 5) via the network interface 140. In this manner, the measurement control unit 203 causes the target person to assume a particular posture.

The measurement control unit 203 sets the cuff pressure at the reference venous pressure by increasing the cuff internal pressure of the cuff 111 that is attached to the upper arm of the target person who assumes the particular posture and detects a cuff pulse wave. The measurement control unit 203 detects a venous pulse by extracting it from the cuff pulse wave by a known method. A time during which to detect a venous pulse may be set at a time in which at least one heartbeat occurs. For example, the measurement control unit 203 can extract a venous pulse from a cuff pulse wave by a known pattern matching method.

When a venous pulse has been detected, the measurement control unit 203 can further vary the cuff pressure from the reference venous pressure and estimate that a cuff pressure at which the venous pulse amplitude takes a maximum value is a central venous pressure.

If a venous pulse is not detected by the measurement control unit 203, the estimation unit 204 estimates that the central venous pressure of the target person is lower than the reference venous pressure. If a venous pulse is detected by the measurement control unit 203, the estimation unit 204 can estimate that the central venous pressure of the target person is higher than or equal to the reference venous pressure.

If a central venous pressure is estimated by the measurement control unit 203 by varying the cuff pressure from the reference venous pressure, the estimation unit 204 can newly estimate whether the estimated central venous pressure is higher than or equal to the reference venous pressure by comparing the estimated central venous pressure with the reference venous pressure.

The display control unit 205 displays a result of estimation by the estimation unit 204 on the display 131. That is, the display control unit 205 displays whether the central venous pressure of the target person is lower than or higher than or equal to the reference venous pressure. The display control unit 205 may output a result of estimation of the estimation unit 204 in the form of a voice that is output from the speaker 132. Alternatively, the display control unit 205 may output (transmit) a result of estimation of the estimation unit 204 to, for example, an external terminal via the network interface 140.

Figure 8:
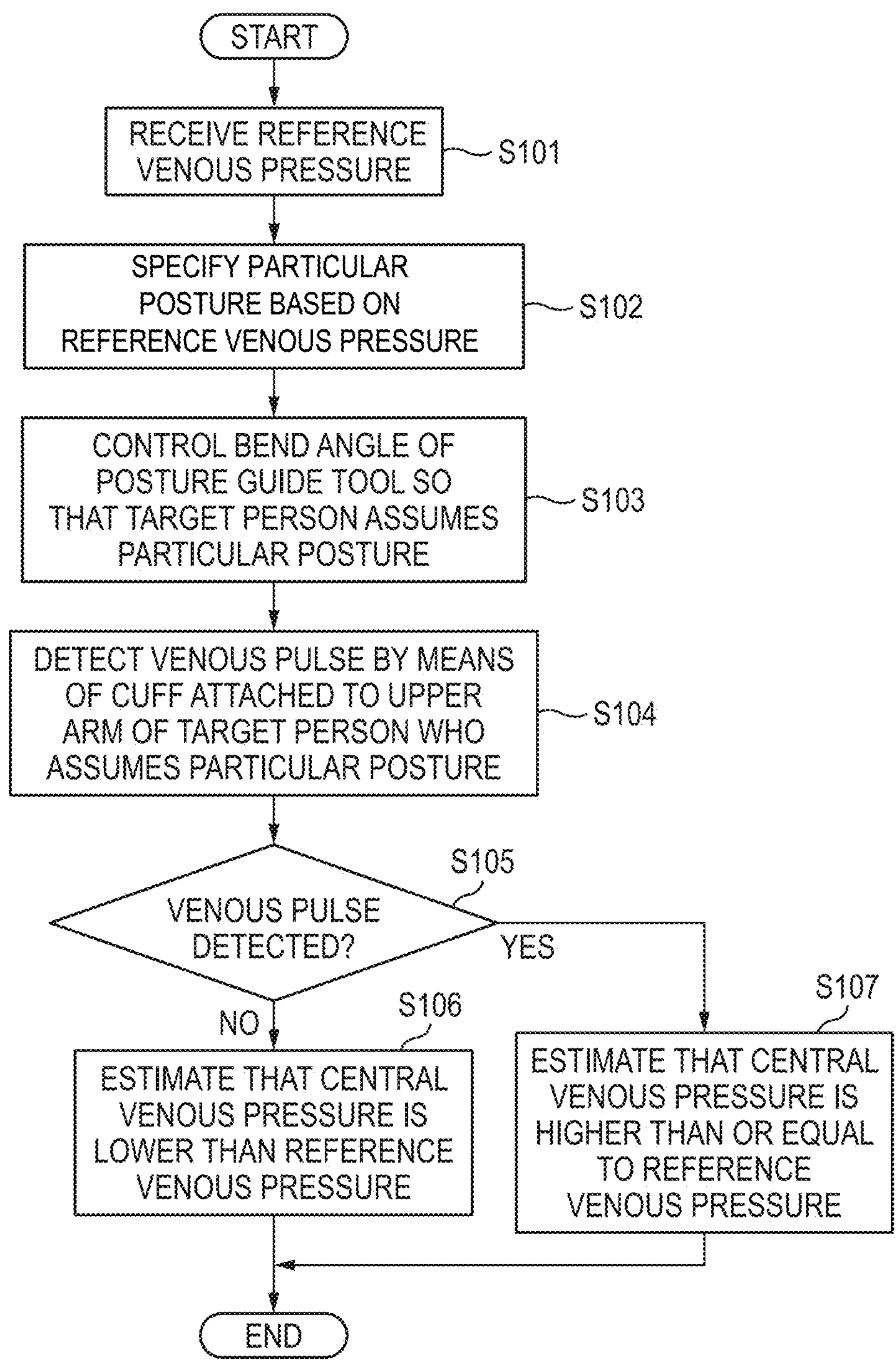
FIG. 8 is a flowchart illustrating how the venous pressure testing system operates.

FIG. 8 is a flowchart illustrating how the venous pressure testing system 100 operates. This flowchart is followed by the control unit 150 according to programs stored in the auxiliary storage unit 153.

The control unit 150 receives a reference venous pressure (a reference venous pressure value) that has been input to the input unit 120 by a user (S101).

The control unit 150 specifies a particular posture based on the reference venous pressure (S102).

The control unit 150 controls the bend angle of the posture guide tool 300 so that a target person assumes the particular posture (S103). The method for causing the target person to assume the particular posture is not restricted to this method. For example, the control unit 150 may guide the target person so that he or she will assume the particular posture by displaying the particular posture (e.g., an angle formed by the upper part and the lower part of the body) on the display 131 or causing the speaker 132 to output a voice indicating the particular posture.

The control unit 150 sets, at the reference venous pressure, the cuff pressure and detects a venous pulse by means of the cuff 111 attached to an upper arm of the target person who assumes the particular posture (S104).

The control unit 150 judges whether a venous pulse is detected (S105). If judging that a venous pulse is not detected (S105: no), the control unit 150 estimates that the central venous pressure of the target person is lower than the reference venous pressure (S106).

If judging that a venous pulse is detected (S105: yes), the control unit 150 estimates that the central venous pressure of the target person is higher than or equal to the reference venous pressure (S107).

(Modification 1)

Figure 9:
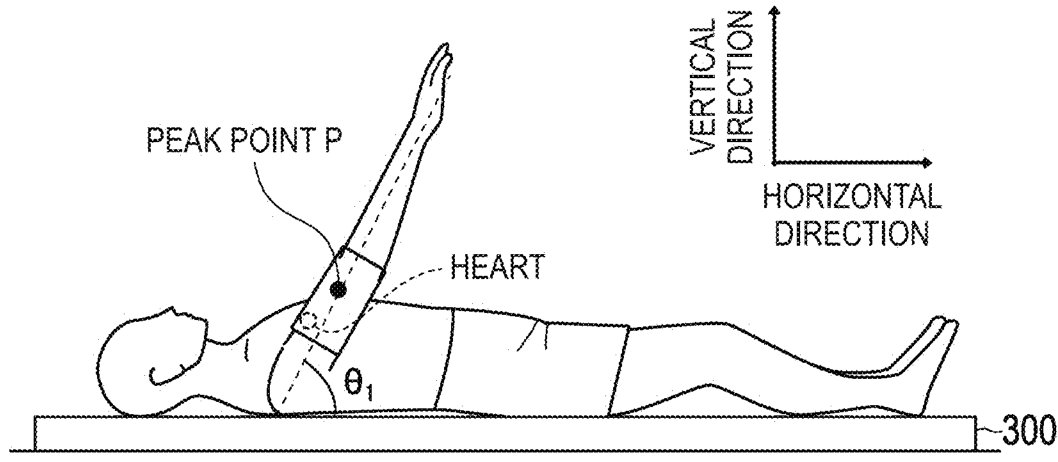
FIG. 9 illustrates an example modified particular posture.

FIG. 9 illustrates an example modified particular posture.

As shown in FIG. 9, the specification unit 202 can specify, as a particular posture, an angle $\theta_1$ formed by the upper part of the body and an upper arm of a target person who is lying on his or her back with his or her upper arm raised higher than the heart toward the vertical direction.

In the example of FIG. 9, the peak point P is a measurement position at which the cuff 111 is attached. A vertical distance is a height of the peak point P in the vertical direction minus a height of the heart in the vertical direction (it corresponds to a distance from the back to the heart). A height of the peak point P in the vertical direction can be calculated based on a distance from the shoulder joint to the attachment position of the cuff 111 and an angle $\theta_1$ formed by the upper part of the body and the upper arm. The distance from the shoulder joint to the attachment position of the cuff 111 and the distance from the back to the heart can be measured in advance, stored in the auxiliary storage unit 153, and used. The specification unit 202 specifies an angle $\theta_1$ indicating a vertical distance corresponding to a reference venous pressure.

(Modification 2)

Figure 10:
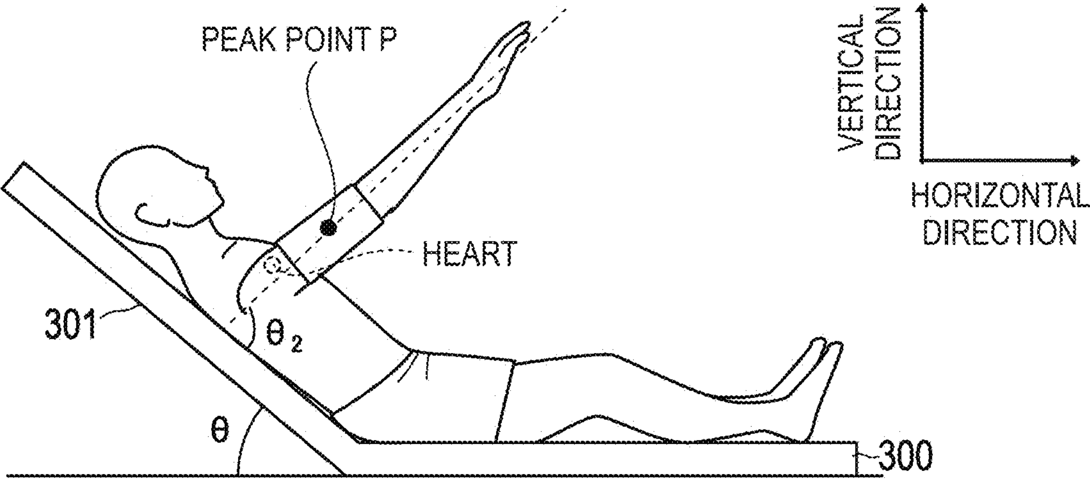
FIG. 10 illustrates another example modified particular posture.

FIG. 10 illustrates another example modified particular posture.

As shown in FIG. 10, the specification unit 202 can specify, as a particular posture, an angle θ formed by the upper part and the lower part of the body of a target person who has raised an upper arm higher than the heart toward the vertical direction and an angle θ2 formed by the upper arm and the upper part of the body.

In the example of FIG. 10, as in Modification 1, the peak point P is a measurement position at which the cuff 111 is attached. A vertical distance is a height of the peak point P in the vertical direction minus a height of the heart in the vertical direction. The vertical distance can be calculated based on a distance from the back to the heart, a distance from the shoulder joint to the attachment position of the cuff 111, an angle θ formed by the upper part and the lower part of the body, and an angle $\theta_2$ formed by the upper arm and the upper part of the body. The distance from the shoulder joint to the attachment position of the cuff 111 and the distance from the back to the heart can be measured in advance, stored in the auxiliary storage unit 153, and used. The specification unit 202 specifies angles θ and $\theta_2$ that indicate a vertical distance corresponding to a reference venous pressure.

(Modification 3)

A venous pulse in an upper arm can be detected using another sensor for measuring a venous pulse in place of the cuff 111, the booster pump 112, the exhaust valve 113, the pressure sensor 114, and the cuff pressure detection unit 115 which are employed in the first embodiment. The other sensor can be a sensor that detects a venous pulse by detecting a physical quantity of at least one of light, an electrical impedance, and an ultrasonic wave. The place where the other sensor is attached to the body of a target person is not limited as long as a venous pulse can be detected there. For example, the other sensor can be attached to one of the arms and legs.

Whereas the above examples are such that the angle of the posture guide tool 300 is changed, the system may operate with a prerequisite that a target person has already assumed a particular posture. That is, the above-described steps S102 and S103 may be omitted. Where it is known that a target person is in a particular posture (e.g., it is known that a target person is in such a posture that the above-mentioned angle θ is equal to 30°), it is not necessary to detect an angle θ formed by the upper part and the lower part of the body of the target person. Furthermore, the estimation unit 204 of the control unit 150 need not judge whether the posture (angle θ) of the target person is a particular posture. That is, since in this case it is a prerequisite that the target person has already assumed a particular posture, the estimation unit 204 estimates that a central venous pressure of the target person is lower than a reference venous pressure if a venous pulse is not detected by the measurement control unit 203. If a venous pulse is detected by the measurement control unit 203, the estimation unit 204 estimates that a central venous pressure of the target person is higher than or equal to the reference venous pressure.

Second Embodiment

In the first embodiment, the posture of a target person is guided to a particular posture forcibly by the posture guide tool 300. On the other hand, in this embodiment, the posture of a target person is not restricted, an angle θ formed by the upper part and the lower part of the body of the target person is detected as a posture of the target person by an angle sensor, and a central venous pressure of the target person is estimated based on whether a venous pulse is detected at a measurement position of an upper arm when the target person is in a particular posture. Since this embodiment is the same as the first embodiment in the other points, redundant descriptions will be omitted.

Figure 11:
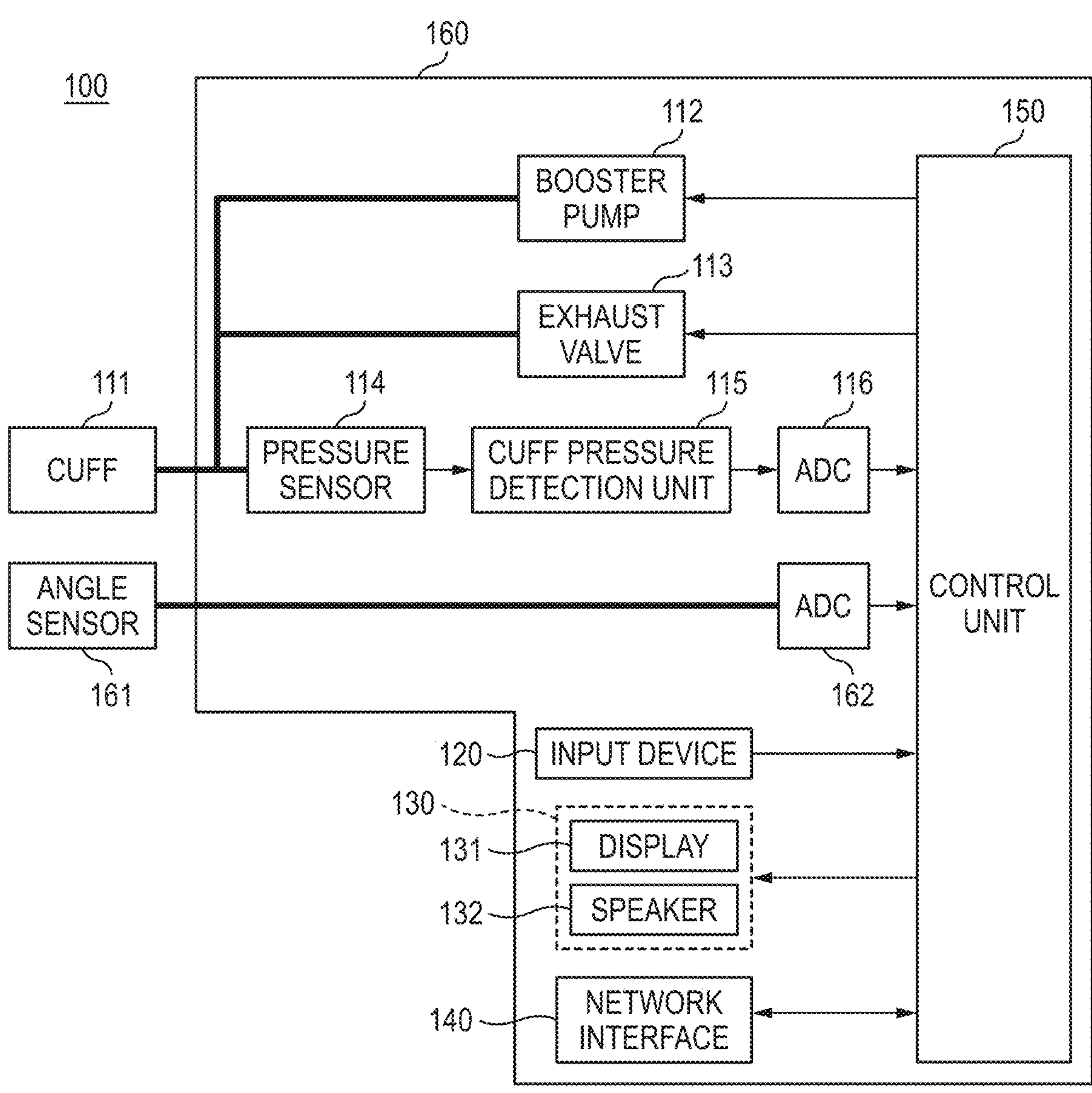
FIG. 11 is a block diagram illustrating a rough hardware configuration of another venous pressure testing system of a Second embodiment.

FIG. 11 is a block diagram illustrating a rough hardware configuration of a venous pressure testing system 100 according to this embodiment.

An angle sensor 161 detects an angle θ formed by the upper part and the lower part of a target person. The angle sensor 161 is part of a posture detection unit. The angle sensor 161 can be an acceleration sensor, for example. The angle sensor 161 outputs the angle θ to an ADC 162 in the form of an analog signal. The ADC 162 converts the analog signal indicating the angle θ into a digital signal and sends the latter to the control unit 150.

The estimation unit 204 (see FIG. 3) of the control unit 150 judges whether a posture (angle θ) of a target person is a particular posture. If a venous pulse is not detected by the measurement control unit 203 when the posture of the target person is judged to be the particular posture, the estimation unit 204 estimates that a central venous pressure of the target person is lower than a reference venous pressure. If a venous pulse is detected by the measurement control unit 203 when the posture of the target person is judged to be the particular posture, the estimation unit 204 estimates that a central venous pressure of the target person is higher than or equal to the reference venous pulse.

The display control unit 205 can display a particular posture on the display 131. Thus, the target person is urged to have his or her posture coincide with the particular posture. This makes it possible to estimate a central venous pressure in a short time.

Third Embodiment

In the first embodiment, a reference venous pressure is received and a particular posture is specified based on the reference venous pressure. On the other hand, in this embodiment, a posture of a target person is received as a particular posture and a reference venous pressure is calculated based on the particular posture. Then whether a central venous pressure of the target person is lower than or higher than or equal to the reference venous pressure based on whether a venous pulse is detected. Since this embodiment is the same as the first embodiment in the other points, redundant descriptions will be omitted.

Figure 12:
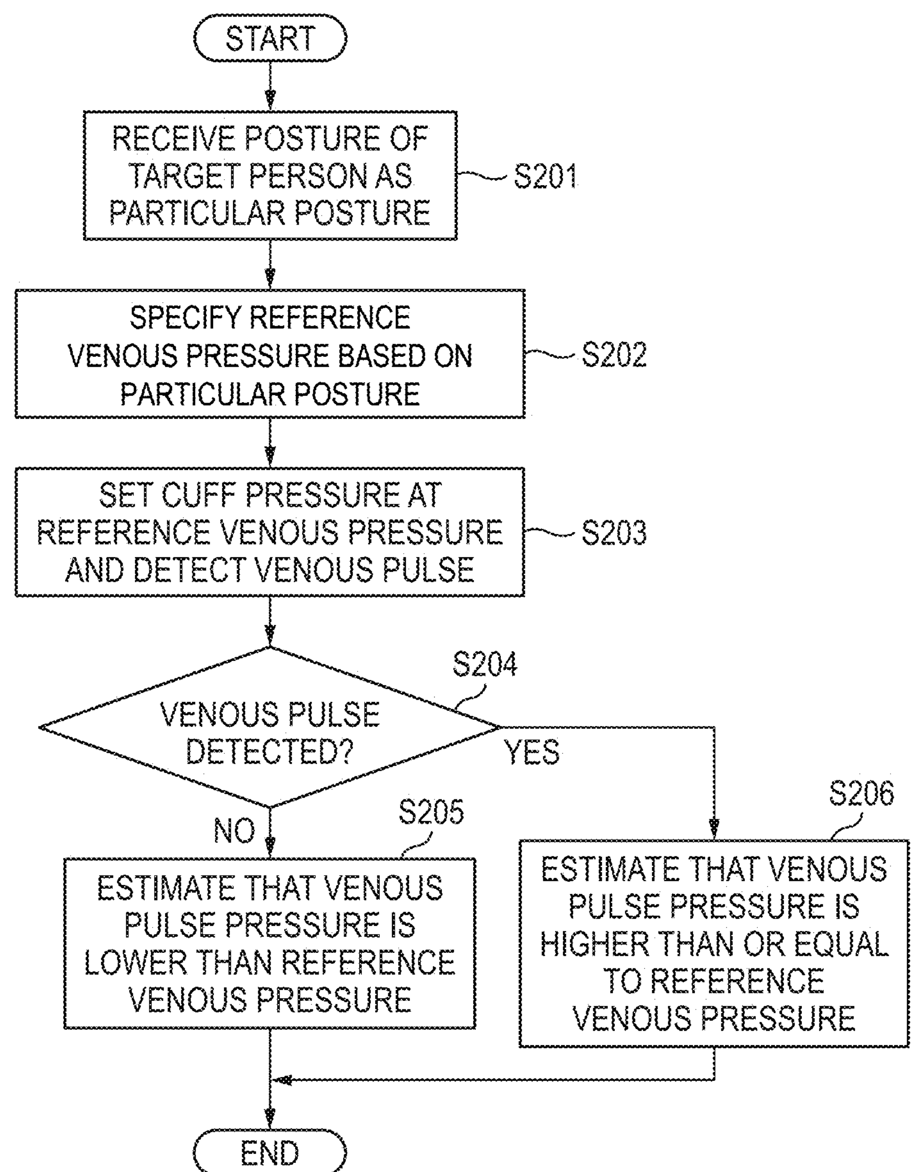
FIG. 12 is a flowchart illustrating how the venous pressure testing system operates.

FIG. 12 is a flowchart illustrating how the venous pressure testing system 100 according to this embodiment operates.

The control unit 150 receives, as a particular posture, a posture of a target person that has been input by a user or the like (S201). For example, the posture of the target person includes an angle formed by the upper part and the lower part of the body of the target person. The control unit 150 may receive a posture of a target person as a particular posture by detecting a posture of the target person.

The control unit 150 calculates a reference venous pressure based on the particular posture (S202). A reference venous pressure can be calculated based on the particular posture by performing an operation that is reverse to the operation by which a particular posture is calculated from a reference venous pressure in the first embodiment.

The control unit 150 sets the cuff pressure at the reference venous pressure using the cuff 111 that is attached to an upper arm of the target person and detects a venous pulse (S203).

The control unit 150 judges whether a venous pulse is detected (S204). If judging that a venous pulse is not detected (S204: no), the control unit 150 estimates that the central venous pressure of the target person is lower than the reference venous pressure (S205).

If judging that a venous pulse is detected (S204: yes), the control unit 150 estimates that the central venous pressure of the target person is higher than or equal to the reference venous pressure (S206). The estimation result can be, for example, displayed on the display 131 together with the calculated reference venous pressure.

The embodiments provide the following advantages.

Presence/absence of a venous pulse is detected at a predetermined measurement position of a target person who assumes a particular posture with which a water-gauge pressure corresponding to a vertical distance between the heart and a peak point, in the vertical direction, of a vein leading from the heart to the predetermined measurement position coincides with a predetermined reference venous pressure. If a venous pulse is not detected, it is estimated that a central venous pressure is lower than the reference venous pressure. This estimation makes it possible to estimate quickly whether a central venous pressure is lower than an optional reference value merely by pressing a target person who assumes the particular posture for a time corresponding to only about one heartbeat. That is, whether circulatory dynamics of a target person is good or bad can be recognized merely by performing, for a short time, cuff pressurization which is very low in invasiveness.

Furthermore, it is estimated that a central venous pressure of the target person is higher than or equal to the reference venous pressure if a venous pulse is detected by the sensor at the measurement position of the target person who assumes the particular posture. This makes it possible to estimate quickly whether a central venous pressure is higher than or equal to an optional reference value.

Furthermore, the reference venous pressure is received and the particular posture of the target person is specified based on the received reference venous pressure. This makes it possible to estimate, flexibly and quickly, whether a central venous pressure is higher than or equal to or lower than an optional reference value.

Moreover, the predetermined measurement position is an upper arm the sensor is a cuff. It is estimated that a central venous pressure of the target person is lower than the reference venous pressure if a venous pulse is not detected by the cuff that is attached to the upper arm of the target person and the cuff pressure of which is set at the reference venous pressure. It is estimated that a central venous pressure of the target person is higher than or equal to the reference venous pressure if a venous pulse is detected by the cuff. This makes it possible to estimate more easily whether a central venous pressure is higher than or equal to or lower than an optional reference value.

Furthermore, an angle formed by the upper part and the lower part of the body of the target person whose arms hang down is specified as the particular posture. This makes it possible to lower the load, imposed on the target person, of estimation of a central venous pressure.

Furthermore, an angle formed by the upper part of the body and an upper arm of the target person who lies on his or her back with the upper arm raised toward the vertical direction is specified as the particular posture. This makes it possible to lower the load, imposed on the target person, of estimation of a central venous pressure.

Furthermore, an angle formed by the upper part and the lower part of the body of the target person who has raised an upper arm above the heart toward the vertical direction and an angle formed by the upper arm and the upper part of the body are specified as the particular posture. This makes it possible to lower the load, imposed on the target person, of estimation of a central venous pressure.

Still further, the cuff pressure is varied from the reference venous pressure and a cuff pressure obtained when the venous pulse has a maximum amplitude is estimated to be a central venous pressure. This makes it possible to increase the accuracy of estimation of a reference venous pressure.

Furthermore, the target person is caused to assume the particular posture by setting a bend angle of a back contact surface, being in contact with the back of the target person, of a posture guide tool capable of adjusting the angle formed by the upper part and the lower part of the body of the target person by bending the back contact surface, at the angle formed by the upper part and the lower part of the body. This makes it possible to further lower the load, imposed on the target person, of estimation of a central venous pressure.

Furthermore, the particular posture is specified based on a length of a line segment drawn on a body surface of the target person so as to connect respective points corresponding to the heart and the peak point and an angle formed by the line segment and a horizontal direction. This makes it possible to estimate a central venous pressure easily with high accuracy.

A display unit which displays the particular posture is provided further. This makes it possible to estimate a central venous pressure in a short time by urging the target person to change his or her posture so that it coincides with the displayed particular posture.

Moreover, body information of the target person is received and the length of the line segment drawn on the body surface of the target person so as to connect the respective points corresponding to the heart and the peak point is calculated based on the received body information. This makes it possible to lower the load, imposed on the target person, of estimation of a central venous pressure.

Furthermore, an angle formed by the upper part and the lower part of the body of the target person is detected as a posture of the target person based on an output of an angle sensor which detects an angle formed by the upper part and the lower part of the body of the target person. It is estimated that a central venous pressure of the target person is lower than the reference venous pressure if a venous pulse is not detected when the detected posture is the particular posture. This makes it possible to further lower the load, imposed on the target person, of estimation of a central venous pressure.

Although the embodiments of the presently disclosed subject matter have been described above in detail, the presently disclosed subject matter is not limited to the above-described embodiments.

For example, all or part of the functions realized by the programs in each of the above-described embodiments can be implemented by hardware such as circuits.

Furthermore, part of the steps of each of the above-described flowcharts may be omitted and another or other steps may be added. Part of the steps may be executed at the same time and one step may be executed in such a manner as to be divided into plural steps.

According to the above disclosure, presence/absence of a venous pulse is detected at a predetermined measurement position of a target person who assumes a particular posture with which a water-gauge pressure corresponding to a vertical distance between the heart and a peak point, in the vertical direction, of a vein leading from the heart to the measurement position coincides with a prescribed reference venous pressure. If a venous pulse is not detected, it is estimated that a central venous pressure is lower than the reference venous pressure. This makes it possible to estimate quickly whether a central venous pressure is lower than an optional reference value.

What is claimed is:

1. A venous pressure testing apparatus for estimating a central venous pressure of a target person by measuring a venous pulse by a cuff sensor at a predetermined measurement position of the target person, comprising:

at least one processor configured to estimate that the central venous pressure of the target person is lower than a predetermined reference venous pressure if the venous pulse is not detected by the cuff sensor at the predetermined measurement position of the target person, wherein the target person has a particular posture, wherein the reference venous pressure coincides with a hydrostatic pressure corresponding to an elevation difference between the heart of the target person and a peak elevation of a vein, wherein the vein leads from the heart to the measurement position, and wherein the at least one processor is configured to set a cuff pressure of the cuff sensor at the reference venous pressure.

2. The venous pressure testing apparatus according to claim 1, wherein the at least one processor is configured to estimate that the central venous pressure of the target person is higher than or equal to the reference venous pressure if the venous pulse is detected by the cuff sensor at the measurement position of the target person who assumes the particular posture.

3. The venous pressure testing apparatus according to claim 2, wherein the at least one processor is configured to:

receive the reference venous pressure; and specify the particular posture of the target person based on the received reference venous pressure.

4. The venous pressure testing apparatus according to claim 3, wherein the particular posture is an angle formed by an upper part and a lower part of a body of the target person whose arms hang down.

5. A venous pressure testing apparatus for estimating a central venous pressure of a target person by measuring a venous pulse by a sensor at a predetermined measurement position of the target person, comprising:

at least one processor configured to estimate that the central venous pressure of the target person is lower than a received predetermined reference venous pressure if the venous pulse is not detected by the sensor at the predetermined measurement position of the target person, wherein the target person has a particular posture, wherein the reference venous pressure coincides with a hydrostatic pressure corresponding to an elevation difference between the heart of the target person and a peak elevation of a vein, wherein the vein leads from the heart to the measurement position wherein the at least one processor estimates that the central venous pressure of the target person is higher than or equal to the reference venous pressure if the venous pulse is detected by the sensor at the measurement position of the target person who assumes the particular posture, wherein the particular posture of the target person is specified based on the received reference venous pressure, wherein the particular posture is an angle formed by an upper part and a lower part of a body of the target person whose arms hang down, and wherein the at least one processor is configured to cause the target person to assume the particular posture by setting a bend angle of a back contact surface, the back contact surface being in contact with the back of the target person, of a posture guide tool capable of adjusting the angle formed by the upper part and the lower part of the body of the target person by bending the back contact surface, at the angle formed by the upper part and the lower part of the body of the target person that has been specified as the particular posture by the specification unit.

6. The venous pressure testing apparatus according to claim 4, wherein the at least one processor is configured to specify the particular posture based on a length of a line segment drawn on a body surface of the target person so as to connect respective points corresponding to the heart and the peak point and an angle formed by the line segment and a horizontal direction.

7. The venous pressure testing apparatus according to claim 6, wherein the at least one processor is configured to:

receive body information of the target person; and calculate the length of the line segment drawn on the body surface of the target person so as to connect the respective points corresponding to the heart and the peak point based on the received body information.

8. The venous pressure testing apparatus according to claim 4, wherein the at least one processor is configured to:

detect an angle formed by the upper part and the lower part of the body of the target person as a posture of the target person based on an output of an angle sensor which detects an angle formed by the upper part and the lower part of the body of the target person; and estimate that the central venous pressure of the target person is lower than the reference venous pressure if the venous pulse is not detected by the sensor at the measurement position of the target person when the detected posture is the particular posture.

9. The venous pressure testing apparatus according to claim 3, wherein the particular posture is an angle formed by an upper part of a body and an upper arm of the target person who lies on his or her back with the upper arm raised toward the vertical direction.

10. The venous pressure testing apparatus according to claim 3, wherein the particular posture is an angle formed by an upper part and a lower part of the body of the target person who has raised an upper arm above the heart toward the vertical direction and an angle formed by the upper arm and the upper part of the body.

11. The venous pressure testing apparatus according to claim 3, further comprising a display unit which displays the particular posture.

12. The venous pressure testing apparatus according to claim 2, wherein:

the measurement position is an upper arm; and the at least one processor is configured to estimate that the central venous pressure of the target person is lower than the reference venous pressure if the venous pulse is not detected by the cuff that is attached to the upper arm of the target person and the cuff pressure of which is set at the reference venous pressure, and estimate that the central venous pressure of the target person is higher than or equal to the reference venous pressure if the venous pulse is detected by the cuff.

13. The venous pressure testing apparatus according to claim 12, wherein the at least one processor is configured to vary the cuff pressure from the reference venous pressure and estimates that a cuff pressure obtained when the venous pulse has a maximum amplitude is a central venous pressure.

14. A non-transitory computer readable storage medium that stores a venous pressure testing program for testing a central venous pressure of a target person by measuring a venous pulse by a cuff sensor at a predetermined measurement position of the target person, the venous pressure testing program causing a computer to execute processing of:

estimating that the central venous pressure of the target person is lower than a predetermined reference venous pressure if the venous pulse is not detected by the cuff sensor at the measurement position of the target person who assumes a particular posture with which a water-gauge pressure corresponding to a vertical distance between the heart of the target person and a peak point, in the vertical direction, of a vein leading from the heart to the measurement position coincides with the reference venous pressure; and setting a cuff pressure of the cuff sensor at the reference venous pressure.

15. A venous pressure testing method for estimating a central venous pressure of a target person by measuring a venous pulse by a cuff sensor at a predetermined measurement position of the target person, comprising:

an estimation step of estimating that the central venous pressure of the target person is lower than a predetermined reference venous pressure if the venous pulse is not detected by the cuff sensor at the measurement position of the target person who assumes a particular posture with which a water-gauge pressure corresponding to a vertical distance between the heart of the target person and a peak point, in the vertical direction, of a vein leading from the heart to the measurement position coincides with the reference venous pressure; and a step of setting a cuff pressure of the cuff sensor at the reference venous pressure.

* * * * *